United States Patent
Fortin

(10) Patent No.: US 11,166,933 B2
(45) Date of Patent: Nov. 9, 2021

(54) POLYUNSATURATED FATTY ACID MONOGLYCERIDES, COMPOSITIONS, METHODS AND USES THEREOF

(71) Applicant: SCF PHARMA INC., Sainte-Luce (CA)

(72) Inventor: Samuel C. Fortin, Sainte-Luce (CA)

(73) Assignee: SCF PHARMA INC., Sainte-Luce (CA)

( * ) Notice: Subject to any disclaimer, the term of this patent is extended or adjusted under 35 U.S.C. 154(b) by 0 days.

(21) Appl. No.: 17/052,302

(22) PCT Filed: May 3, 2019

(86) PCT No.: PCT/CA2019/050587
§ 371 (c)(1),
(2) Date: Nov. 2, 2020

(87) PCT Pub. No.: WO2019/210424
PCT Pub. Date: Nov. 7, 2019

(65) Prior Publication Data
US 2021/0161853 A1    Jun. 3, 2021

Related U.S. Application Data

(60) Provisional application No. 62/666,375, filed on May 3, 2018.

(51) Int. Cl.
*A61K 31/232* (2006.01)
*A61P 1/14* (2006.01)

(52) U.S. Cl.
CPC .............. *A61K 31/232* (2013.01); *A61P 1/14* (2018.01)

(58) Field of Classification Search
CPC .................... A61K 31/23; A61P 1/14
See application file for complete search history.

(56) References Cited

U.S. PATENT DOCUMENTS

| | | |
|---|---|---|
| 6,180,671 B1 | 1/2001 | Freedman et al. |
| 6,552,081 B1 | 4/2003 | Freedman et al. |
| 7,138,431 B1 | 11/2006 | Chilton |
| 7,981,915 B2 | 7/2011 | Freedman |
| 8,119,690 B2 | 2/2012 | Fortin |
| 8,198,324 B2 | 6/2012 | Fortin |
| 8,222,295 B2 | 7/2012 | Fortin |
| 8,329,747 B2 | 12/2012 | Fortin |
| 8,722,737 B2 | 5/2014 | Fortin |
| 8,816,110 B2 | 8/2014 | Fortin |
| 9,101,563 B2 | 8/2015 | Fortin |
| 9,233,915 B2 | 1/2016 | Fortin |
| 9,447,020 B2 | 9/2016 | Fortin |
| 9,480,660 B2 | 11/2016 | Fortin |
| 9,670,133 B2 | 6/2017 | Koch et al. |
| 9,925,165 B2 | 3/2018 | Fortin |

(Continued)

FOREIGN PATENT DOCUMENTS

| | | |
|---|---|---|
| CA | 2538382 | 3/2005 |
| CA | 2599473 | 9/2006 |

(Continued)

OTHER PUBLICATIONS

Png et al. (Am J Gasteroenterol, 2010, 105, p. 2420-28). (Year: 2010).*
Turmeric—The Genus Curcuma, Edited by P.N. Ravindran et al., Jul. 24, 2006.
Akoh, "Lipase-Catalyzed Synthesis or Partial Glyceride", Biotechnology Letters, vol. 15, No. 9 (Sep. 1993) pp. 949-954.
Ando et al., "Reinvestigation of Positional Distribution of Fatty Acids in Docosahexaenoic Acid-Rich Fish Oil Triacyl-sn-glycerols". Lipids, vol. 35, No. 5 (2000) pp. 579-582.
Beharry et al., "Long-term docosahexaenoic acid therapy in a congenic murine model of cystic fibrosis", Am J Physiol Gastrointest Liver Physiol 292:G839-G848, 2007 First Published Nov. 9, 2006.

(Continued)

*Primary Examiner* — Umamaheswari Ramachandran
(74) *Attorney, Agent, or Firm* — Bereskin & Parr LLP/S.E.N.C.R.L., s.r.l.

(57) ABSTRACT

There are provided various compounds and compositions comprising polyunsaturated fatty acid monoglycerides and derivatives thereof. These compounds and compositions can be useful for use as prebiotic in a subject; for the modulation of the microbiota composition; for enhancing the population of good bacteria like *Akkermansia muciniphila* and for enhancing the efficacy of cancer immunotherapy of a subject. These compounds and compositions comprise at least one compound chosen from formula (I), (II), (III), (IV).

(I)

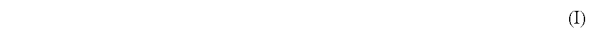

(II)

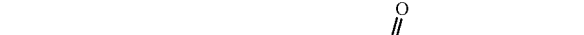

(III)

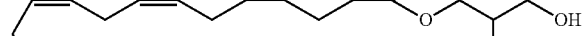

(IV)

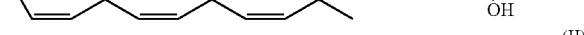

14 Claims, 2 Drawing Sheets

(56) References Cited

U.S. PATENT DOCUMENTS

| | | | |
|---|---|---|---|
| 10,716,776 | B2 | 7/2020 | Fortin |
| 2002/0188024 | A1 | 12/2002 | Chilton et al. |
| 2004/0214799 | A1 | 10/2004 | Mukai et al. |
| 2006/0121583 | A1 | 6/2006 | Lassalle et al. |
| 2009/0291102 | A1 | 11/2009 | Fortin |
| 2009/0292019 | A1 | 11/2009 | Fortin |
| 2010/0160261 | A1 | 6/2010 | Fortin |
| 2010/0196496 | A1 | 8/2010 | Fortin |
| 2012/0213872 | A1 | 8/2012 | Fortin |
| 2012/0251582 | A1 | 10/2012 | Fortin |
| 2013/0059911 | A1 | 3/2013 | Fortin |
| 2015/0119591 | A1 | 4/2015 | Fortin |
| 2015/0343071 | A1 | 12/2015 | Vangara et al. |
| 2017/0049830 | A1 | 2/2017 | Raderman |
| 2018/0078504 | A1 | 3/2018 | Sacks et al. |
| 2018/0264121 | A1 | 9/2018 | Donaduzzi et al. |
| 2019/0133992 | A1 | 5/2019 | Shaaban |
| 2019/0231833 | A1 | 8/2019 | Garti et al. |
| 2019/0314326 | A1 | 10/2019 | Garti et al. |
| 2019/0374502 | A1 | 12/2019 | Jha |
| 2020/0121606 | A1 | 4/2020 | Sacks et al. |
| 2020/0316007 | A1 | 10/2020 | Fortin |

FOREIGN PATENT DOCUMENTS

| | | |
|---|---|---|
| EP | 1352648 | 10/2003 |
| JP | 2010132631 | 6/2010 |
| WO | 2002064166 | 8/2002 |
| WO | 2002089787 | 11/2002 |
| WO | 2002096408 | 12/2002 |
| WO | 2004000333 | 12/2003 |
| WO | 2004024136 | 3/2004 |
| WO | 2004064716 | 8/2004 |
| WO | 2006117668 | 11/2006 |
| WO | 2008036353 | 3/2008 |
| WO | 2015063041 | 5/2015 |
| WO | 2016066460 | 5/2016 |
| WO | 2017216362 | 12/2017 |
| WO | 2019234728 | 12/2019 |
| WO | 2020028991 | 2/2020 |
| WO | 2020044118 | 3/2020 |
| WO | 2021022378 | 2/2021 |

OTHER PUBLICATIONS

Chau et al., "Monoglyceride and diglyceride lipases from human platelet microsomes", Biochimica et Biophysica Acta, 963 (Jun. 1988) 436-444.

Duvoix et al., "Chemopreventive and therapeutic effects of curcumin", Cancer Letters 223 (2005) 181-190.

English Abstract of JP02131418, "Comparison of enhanced and routine methods for measuring ambient low-level sulfur dioxide", published on May 21, 1990.

English Abstract of JP7149786, "Glyceroglycolipid and Carcinogenic Promoter Inhibitor" published on Jun. 13, 1995.

English Abstract of JP62077319, "Anticancer pharmaceuticals containing eicosapentaenoic acid, its esters, or glycerides", published on Apr. 9, 1987.

English Abstract of JP2000044588, "Novel monoacylglycosyl monoacylglycerols for surfactants", published on Feb. 15, 2000.

Li et al., "Biosynthesis of Docosahexaenoate-Containing Glycrolipid Molecular Species in the Retina", Journal of Molecular Neuroscience, vol. 16, Nov. 1, 2001.

Freedman et al., "Fatty acids in cystic fibrosis", Current Opinion in Pulmonary Medicine 2000, 6:530-532.

Kafrawy et al., "Docosahexaenoic acid in phosphatidylcholine mediates cytotoxicity more effectively than other ω-3 and ω-6 fatty acids", Cancer Letters 132 (May 19, 1998) 23-29.

Kawashima et al., "Inhibition of Rat Liver Microsomal Desaturases by Curcumin and Related Compounds", Biosci. Biotech Biochem 60 (1), 108-110, 1996.

Kawashima et al., "Nicardipine and Nifedipine Inhibit Fatty Acid Desaturases in Rat Liver Microsomes", Biosci. Biotech. Biochem., 60 (10), 1672-1676, 1996.

Kawashima et al., "Inhibotory effects of alkyl and its derivatives on fatty acid desaturation", Biochimica et Biophysica Acta 1299 (1996) 34-38.

Kawashima et al., "Enzymatic Synthesis of High-Purity Structured Lipids with Caprylic Acid at 1,3-Positions and Polyunsaturated Fatty Acid at 2-Position", JAOCS, vol. 78, No. 6 (2001).

Martin et al., "The safety and efficacy of oral docosahexaenoic acid supplementation for the treatment of primary sclerosing cholangitis—a pilot study", Aliment Pharmacol Ther 2012; 35: 255-265.

Monks et al., "Feasibility of a High-Flux Anticancer Drug Screen Using a Diverse Panel of Cultured Human Tumor Cell Lines", Articles, vol. 83, No. 11, Jun. 5, 1991.

Abstract of Myrdal et al., "Solubilization of Drugs in Aqueous Media", Encyclopedia of Pharmaceutical Technology, published on Oct. 2, 2006.

Nakano et al., "Inhibitory Effects of Capsaicinoids on Fatty Acid Desaturation in a Rat Liver Cell Line", Biosci. Biotechnol. Biochem., 65 (8), 1859-1863, Mar. 29, 2001.

Ohta et al., Action of a New Mammalian DNA Polymerase Inhibitor, Sulfoquinovosyldiacylglycerol, Biol. Pharm. Bull. 22 (2) 111-116, Feb. 1999.

Pacetti et al., "High performance liquid chormatography-tandem mass spectometry of phospholipid molecular species in eggs from hen fed diets enriched in seal blubber oil", Journal of Chromatography A, 1097 (Aug. 30, 2005) 66-73.

Abstract of Rohan et al., "Dietary factors and survival from breast cancer", Nutr Cancer, 1993;20(2):167-177.

Rose et al., "Omega-3 fatty acids as cancer chemopreventive agents", Pharmacology & Therapeutics 83 (1999) 217-244.

Rosu et al., "Enzymatic synthesis of glycerides from DHA-enriched PUFA ethyl ester by glycerolysis under vacuum", Journal of Molecular Catalysis B: Enzymatic 4 (1998) 191-198.

Rubinstein et al., "Comparison of In Vitro Anticancer-Drug-Screening Data Generated With a Tetrazolium Assay Versus a Protein Assay Against a Diverse Panel of Human Tumor Cell Lines", Articles, vol. 82, No. 13, Jul. 4, 1990.

Schaaf et al., "Polyunsaturated Monoglycerides and a Pregnadiene in Defensive Glands of the Water Beetle Agabus affinis", Lipids, vol. 35, No. 5 (2000).

Shimizu et al., "Sesamin is a Potent and Specific Inhibitor of Δ5 Desaturase in Polyunsaturated Fatty Acid Biosynthesis", Lipids, vol. 26, No. 7 (1991).

Skehan et al., "New Colorimetric Cytotoxicity Assay for Anticancer-Drug Screening", Articles, vol. 82, No. 13, Jul. 4, 1990.

Tanaka et al., "Preparative Separation of Acylglycerol by Centrifugal Partition Chromatography (CPC)", Thermochimica (1990).

Vandevoorde et al., "Influence of the degree of unsaturation of the acyl side chain upon the interaction of analogues of 1-arachdonoylglycerol with monoacylglycerol lipase and fatty acid amid hydrolase", Biochemical and Biophysical Research Communication 337 (Sep. 13, 2005) 104-109.

Watanabe et al., "Chemical signals involved in larval metamorphosis in Hydroides ezoensis (Serpulidae; Polychaeta). Part II: Isolation and identification of a new monoacyl glycerol from adult tube clumps as a metamorphosis-inducing substance", J Mar Biotechnol (1998) 6:11-15.

Watanabe et al., "n-3 Polyunsaturated fatty acid (PUFA) deficiency elevates and n-3 PUFA enrichment reduces brain 2-arachidonoylglycerol level in mice", Prostaglandins, Leukotrienes and Essential Fatty Acids 69 (Mar. 20, 2003) 51-59.

Yamane et al., "Multiple Intensified Performance of an Enzyme-Catalyzed Reaction in Organic Medium", Analysis New York Academy Sciences (1988).

Zerouga et al., "Synthesis of a novel phosphatidylcholine conjugated to docosahexaenoic acid and methotrexate that inhibits cell proliferation", Anti-Cancer Drugs 2002, pp. 301-311.

Debora Cutuli, "Functional and Structural Benefits Induced by Omega-3 Polyunsaturated Fatty Acids During Agin", Current Neuropharmacology, 2017, 15, 534-542.

(56) References Cited

OTHER PUBLICATIONS

English Abstract of JP2010132631A, "Composition Having Inverse Agonist and Antagonist Activities of Cannabicoid Receptor", published on Jun. 17, 2010.
Flachs et al., "Polyunsaturated fatty acids of marine origin upregulate mitochondrial biogenesis and induce β-oxidation in white fat", Diabetologia (Oct. 5, 2005) 48:2365-2375.
Herbst et al., "Omega-3 supplementation alters mitochondrial membrane composition and respiration kinetics in human skeletal muscle", J. Physiol. 592.6 (Jan. 6, 2014) pp. 1341-1352.
Johnson et al., "Eicosapentaenoic acid but not docosahexaenoic acid restores skeletal muscle mitochondrial oxidative capacity in old mide", Aging Cell (2015) 14, pp. 734-743.
Morin et al., "Docosapentaenoic acid monoacylglyceride reduces inflammation and vascular remodeling in experimental pulmonary hypertension", Am J Physiol Heart Circ Physiol 307: H574-H586, Jun. 14, 2014.
Swanson et al., "Omega-3 Fatty Acids EPA and DHA: Health Benefits Throughout Life", American Society for Nutrition. Adv. Nutr. 3: 1-7, 2012.
Alcock et al., "Fatty acids from diet and microbiota regulate energy metabolism" [version 1; referees: 2 approved], F1000 Research 2015, F(F1000 Faculty Rev):738 / Last updated: Sep. 10, 2015.
Constantini et al., "Impact of Omega-3 Fatty Acids on the Gut Microbiota", Int. J. Mol. Sci. Dec. 7, 2017, 18, 2645.
Khaddaj-Mallat et al., "Novel n-3 PUFA monoacylglycerides of pharmacological and medicinal interest: Anti-inflammatory and anti-proliferative effects", European Journal of Pharmacology 792 (Oct. 31, 2016) 70-77.
Piazzi et al., "Eicosapentaenoic acid free fatty acid prevents and suppresses colonic neoplasia in colitis-associated colorectal cancer acting on Notch signaling and gut microbiota", Int. J. Cancer: 135, 2004-2013 (Mar. 19, 2014).
Cockbain et al., "Omega-3 polyunsaturated fatty acids for the treatment and prevention of colorectal cancer", Gut 2012; 61: 135-149 (Published Online First: Apr. 13, 2011).
Barry et al., "Anticancer Agents. IV. 1a,b The antitumor Activity of Some 1,4- and 1,5-(Bisthiosemicarbazones) and of Related Heterocycles" Journal of Meidcinal Chemistry, 1970, vol. 13, No. 3 (Received Sep. 10, 1968).
Liang et al., "Effect of dietary omega-3 fatty acids on tumor-associated macrophages and prostate cancer progression", Prostate, Oct. 2016, 76(14): 1293-1302.
Newell et al., "A Critical Review on the Effect of Docosahexaenoic Acid (DHA) on Cancer Cell Cycle Progression", Int J Mol Sci. Aug. 2017; 18(8): 1784.
Ramsaywack et al., "Synthesis and Surface Investigations of N-Substitued 2,5-Dithio-7-azabicyclo[2. 2.1]heptanes on Gold Surfaces", J. Phys. Chem. C Mar. 16, 2012, 116, 7886-7896.
Shao et al., "Structural characterization of self-assemblies of new omega-3 lipids: docosahexaenoic acid and docosapentaenoic acid monoglycerides", Phys. Chem. Phys., Aug. 31, 2018, 20, 23928.
Vairoletti et al., "Synthesis of bicyclic 1,4-thiazepines as novel anti-Trypanosoma brucei brucei agents", Med. Chem. Commun., Jun. 11, 2019, 10, 1481.
Zgair et al., "Oral administration of cannabis with lipids leads to high levels of cannabinoids in the intestinal lymphatic system and prominent immunomodulation". Scientific Reports, 7:14542, Published online: Nov. 6, 2017.
Zhdanko et al., "One-step synthesis of N-acetylcysteine and glutathione derivatives using the Ugi reaction", Tetrahedron 65 (Apr. 17, 2009) 4692-4702.
Egil Fosslien, "Review: Mitochondrial Meidine—Molecular Pathology of Defective Oxidative Phosphorylation", Annals of Clinical & Laboratory Science, vol. 31, No. 1, 2001, pp. 25-67.
Marsicano et al., "Neuroprotective properties of cannabinoids against oxidative stress: role of the cannabinoid receptor CB1", Journal of Neurochemistry, vol. 80, Issue 3, Jan. 21, 2002.
Abstract of Herrera et al., "The CB2 cannabinoid receptor signals apoptosis via ceramide-dependent activation of the mitochondrial intrinsic pathway", Experimental Cell Research, vol. 312, Issue 11, Jul. 1, 2006, pp. 2121-2131.
Abstract of Athanasiou et al., "Cannabinoid receptor agonists are mitochondrial inhibitors: A unified hypothesis of how cannabinoids modulate mitochondrial function and induce cell death", Biomedical and Biophysical Research Communications, vol. 364, Issue 1, Dec. 7, 2007, pp. 131-137.
Tedesco et al., "Cannabinoid Type 1 Receptor Blockade Promotes Mitochondrial Biogenesis Through Endothelial Nitric Oxide Synthase Expression in White Adipocytes", Diabetes, vol. 57, Aug. 2008.
Davani-Davari et al., "Prebiotics: Definition, Types, Sources, Mechanisms, and Clinical Application", Foods 2019, 8, 92 (Published Mar. 9, 2019).
Gibson et al., "Dietary Modulation of the Human Colonic Microbiota: Introducing the Concept of Prebiotics", MRC Dunn Clinical Nutrition Centre, Cambridge, UK and Unité de Biochimie Toxicologique et Cancérologue, Départment des Sciences Pharmaceutiques, Université Catholique de Louvain, Brussels, Belgium, American Institute of Nutrition 1995. (The year of publication is sufficiently earlier than the effective U.S. filing date so that the particular month of publication is not an issue.)

* cited by examiner

POLYUNSATURATED FATTY ACID MONOGLYCERIDES, COMPOSITIONS, METHODS AND USES THEREOF

CROSS-REFERENCE TO RELATED APPLICATIONS

The present application is a 35 USC 371 national stage entry of PCT/CA2019/050587 filed on May 3, 2019 and which claims priority to U.S. 62/666,375 filed on May 3, 2018. These documents are hereby incorporated herein by reference in their entirety.

FIELD OF THE DISCLOSURE

The present document relates to the field of microbiota. More particularly, it relates to polyunsaturated fatty acid monoglyceride compounds and combinations thereof. It also provided a use as prebiotic and/or a method for modulate the microbiota composition and/or for enhancing the population of at least one probiotic strain. There is also provided a method for enhancing the efficacy of cancer immunotherapy of a subject.

BACKGROUND OF THE DISCLOSURE

The human gut microbiota is not static and can be rapidly modulated by several factors (Faith and al., The long-term stability of the human gut microbiota 2013. Science 341 6141: 1237439). Changes in diet and long-chain omega-3 (LCn3) can modulate the gut microbiota of both healthy and prostate cancer (PCa) patients (Costantini, L. and al., Impact of Omega-3 Fatty Acids on the Gut Microbiota 2017. Int J Mol Sci 18, 12). Daily intake of 4 g LCn3 for 8 weeks was associated with a reversible bacterial signature and eicosapentaneoic acid (EPA) promotes prevalence of anti-inflammatory bacteria like *Lactobacillus* and *Akkermansia* species from the gut microbiota (Piazzi, G. and al., Eicosapentaenoic acid free fatty acid prevents and suppresses colonic neoplasia in colitis-associated colorectal cancer acting on Notch signaling and gut microbiota 2014. Int J Cancer 135(9): 2004-2013).

SUMMARY OF THE DISCLOSURE

According to one aspect there is provided at least one compound chosen from compound of formula (I), compound of formula (II), compound of formula (III) and compound of formula (IV):

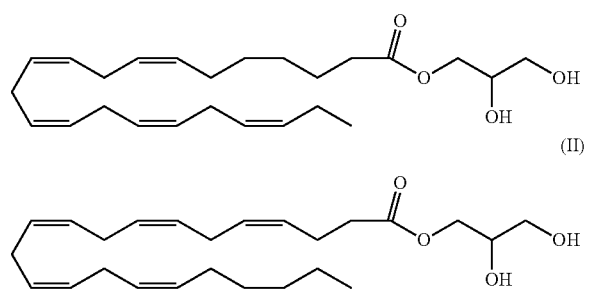

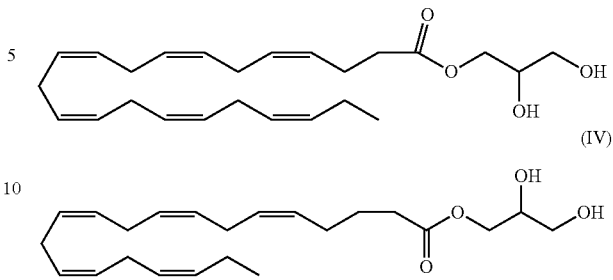

for use as prebiotic in a subject in need thereof.

According to another aspect there is provided at least one compound chosen from compound of formula (I), compound of formula (II), compound of formula (III) and compound of formula (IV) for the modulation of the microbiota composition of a subject in need thereof.

According to another aspect there is provided at least one compound chosen from compound of formula (I), compound of formula (II), compound of formula (III) and compound of formula (IV) for enhancing the population of at least one probiotic strain of a subject in need thereof.

According to another aspect there is provided at least one compound chosen from compound of formula (I), compound of formula (II), compound of formula (III) and compound of formula (IV) for enhancing the efficacy of cancer immunotherapy of a subject in need thereof.

According to another aspect there is provided the use of at least one compound chosen from compound of formula (I), compound of formula (II), compound of formula (III) and compound of formula (IV) for use as prebiotic in a subject in need thereof.

According to another aspect there is provided the use of at least one compound chosen from compound of formula (I), compound of formula (II), compound of formula (III) and compound of formula (IV) for the modulation of the microbiota composition of a subject in need thereof.

According to another aspect there is provided the use of at least one compound chosen from compound of formula (I), compound of formula (II), compound of formula (III) and compound of formula (IV) for enhancing the population of at least one probiotic strain of a subject in need thereof.

According to another aspect there is provided the use of at least one compound chosen from compound of formula (I), compound of formula (II), compound of formula (III) and compound of formula (IV) for enhancing the efficacy of cancer immunotherapy of a subject in need thereof.

According to another aspect there is provided the use of at least one compound chosen from compound of formula (I), compound of formula (II), compound of formula (III) and compound of formula (IV) in the manufacture of a medicament for use as prebiotic in a subject in need thereof.

According to another aspect there is provided the use of at least one compound chosen from compound of formula (I), compound of formula (II), compound of formula (III) and compound of formula (IV) in the manufacture of a medicament for the modulation of the microbiota composition of a subject in need thereof.

According to another aspect there is provided the use of at least one compound chosen from compound of formula (I), compound of formula (II), compound of formula (III) and compound of formula (IV) in the manufacture of a medicament for enhancing the population of at least one probiotic strain of a subject in need thereof.

According to another aspect there is provided the use of at least one compound chosen from compound of formula (I), compound of formula (II), compound of formula (III) and compound of formula (IV) in the manufacture of a medicament for enhancing the efficacy of cancer immunotherapy of a subject in need thereof.

According to another aspect there is provided a method for use as prebiotic in a subject in need thereof comprising administering an effective amount of at least one compound chosen from compound of formula (I), compound of formula (II), compound of formula (III) and compound of formula (IV).

According to another aspect there is provided a method for modulating a microbiota composition of a subject in need thereof comprising administering to the subject an effective amount of at least one compound chosen from compound of formula (I), compound of formula (II), compound of formula (III) and compound of formula (IV).

According to another aspect there is provided a method for enhancing the population of at least one probiotic strain of a subject in need thereof comprising administering to the subject an effective amount of at least one compound chosen from compound of formula (I), compound of formula (II), compound of formula (III) and compound of formula (IV).

According to another aspect there is provided a method for enhancing efficacy of a cancer immunotherapy of a subject in need thereof comprising administering to the subject an effective amount of at least one compound chosen from compound of formula (I), compound of formula (II), compound of formula (III) and compound of formula (IV).

According to another aspect, there is provided a composition comprising:
(i) at least one compound chosen from compound of formula (I), compound of formula (II), compound of formula (III) and compound of formula (IV);
(ii) at least one lipid.

According to another aspect, there is provided a composition comprising (i) at least one compound chosen from compound of formula (I), compound of formula (II), compound of formula (III) and compound of formula (IV) and (ii) at least one lipid for use as prebiotic in a subject in need thereof.

According to another aspect, there is provided a composition comprising (i) at least one compound chosen from compound of formula (I), compound of formula (II), compound of formula (III) and compound of formula (IV) and (ii) at least one lipid for the modulation of the microbiota composition of a subject in need thereof.

According to another aspect, there is provided a composition comprising (i) at least one compound chosen from compound of formula (I), compound of formula (II), compound of formula (III) and compound of formula (IV) and (ii) at least one lipid for enhancing the population of at least one probiotic strain of a subject in need thereof.

According to another aspect, there is provided a composition comprising (i) at least one compound chosen from compound of formula (I), compound of formula (II), compound of formula (Ill) and compound of formula (IV) and (ii) at least one lipid for enhancing the efficacy of cancer immunotherapy of a subject in need thereof.

BRIEF DESCRIPTION OF THE FIGURES

Further features and advantages will become more readily apparent from the following description of specific embodiments as illustrated by way of examples in the appended figures wherein.

DETAILED DESCRIPTION OF THE DISCLOSURE

Figure 1:
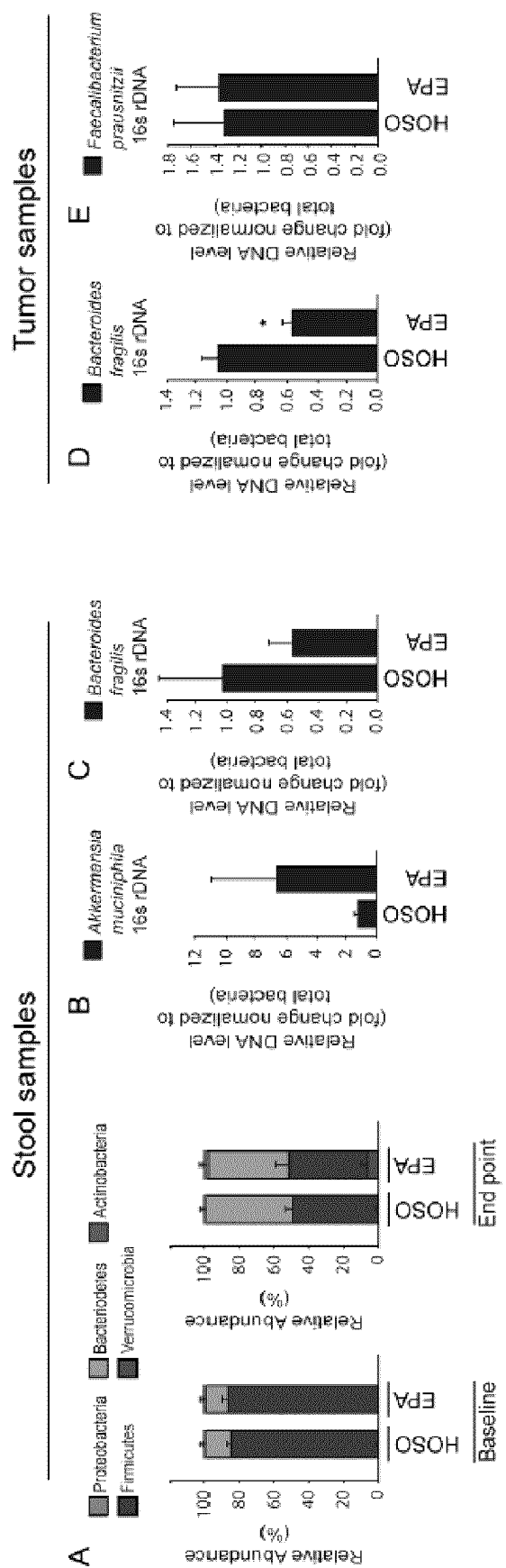
FIG. 1 represents the effect of composition 1 (Eicosapentaenoic acid monoglyceride, MAG-EPA) on gut-derived microbiota (A) and tumor-derived microbiota (B). 16S rDNA was extracted from stool samples and tumors of mice fed with composition 1 or control HOSO (higholeic sunflower oil, n=12/group) for 4 weeks before injection of TRAMP-C2 prostate cancer cells. Daily gavage was continued until animal sacrifice.

Further features and advantages of the previously-mentioned compounds will become more readily apparent from the following description of non-limiting examples.

The term "microbiota" as used herein refers to an "ecological community of commensal, symbiotic and pathogenic microorganisms" found in and on all multicellular organisms. For example, in human the microbiota can refers to whole body microbiota or organ specific microbiota like gut microbiota, prostate microbiota, skin microbiota, etc.

The term "prebiotic" as used herein refers to a food ingredient that induces the growth or activity of beneficial microorganisms (e.g., bacteria and fungi).

The term "lipid" as used herein refers to as any fat-soluble (lipophilic), molecules, such as fats, fat-like substances, oils (such as animal oil, marine oil, vegetable oil, fish oil concentrate, re-esterified fish oil or re-esterified concentrated fish oil), waxes, sterols (such as cholesterol, ergosterol, sitosterol, stigmasterol, fat-soluble vitamins (such as vitamins A, D, E and K), fatty acids, oxidized fatty acid (such as lipoxin, specialized pro-resolving mediators or epoxydes), fatty acids esters thereof, and various derivatives thereof such as monoglycerides, diglycerides, triglycerides, phospholipids, glycolipids, and cerebrosides and pharmaceutically acceptable salts thereof.

The expression "effective amount" of a compound of the present disclosure is a quantity sufficient to, when administered to the subject, including a mammal, for example a human, effect beneficial or desired results, including clinical results, and, as such, an "effective amount" depends upon the context in which it is being applied. The amount of a given compound of the present disclosure that will correspond to such an amount will vary depending upon various factors, such as the given drug or compound, the pharmaceutical formulation, the route of administration, the identity of the subject or host being treated, and the like, but can nevertheless be routinely determined by one skilled in the art.

The term "probiotic strain" as used herein refers to any microorganisms that are known to provide health benefits when consumed. The World Health Organization's (WHO) 2001 defines probiotics as live microorganisms that, " . . . when administered in adequate amounts, confer a health benefit on the host".

For example, the subject in need thereof can be a bee, human, cat, dog, etc. . . . .

For example, the at least one compound is said compound of formula (I).

For example, the at least one compound is said compound of formula (II).

For example, the at least one compound is said compound of formula (III).

For example, the at least one compound is said compound of formula (IV).

For example, the at least one compound is said compound of formula (I), said compound of formula (III) and said compound of formula (IV).

For example, the at least one compound is said compound of formula (I) and said compound of formula (IV).

For example, the at least one compound is said compound of formula (I) and said compound of formula (III).

For example, the at least one compound is said compound of formula (III) and said compound of formula (IV).

For example, the at least one compound can be for use in combination with at least one lipid.

For example, the at least one lipid and said at least one compound can be for simultaneous administration.

For example, the at least one lipid and said at least one compound can be for separate administration.

For example, the at least one compound chosen from compound of formula (I), compound of formula (II), compound of formula (III) and compound of formula (IV) can be administered in combination with at least one lipid.

For example, the at least one lipid and said at least one compound can be administered simultaneously.

For example, the at least one lipid and said at least one compound can be administered separately.

For example, the at least one lipid can be chosen from animal oil, marine oil, fish oil, fish oil concentrate, re-esterified fish oil, re-esterified concentrated fish oil, vegetable oil, fatty acids, fatty acids ethyl esters, fatty acids esters, monoglycerides, diglycerides, triglycerides and phospholipids.

For example, the at least one lipid can be chosen from marine oil, fish oil, fish oil concentrate, re-esterified fish oil, re-esterified concentrated fish oil, fatty acids ethyl esters, fatty acids esters, monoglycerides, diglycerides, triglycerides and phospholipids.

For example, the at least one probiotic strain can be chosen from *Akkermansia muciniphila, Bacillus coagulans, Bifidobacterium animalis, Bifidobacterium bifidum, Bifidobacterium breve, Bifidobacterium longum, Lactobaccilus acidophilus, Lactobacillus bulgaricus, Lactobacillus rhamnosus, Lactobacillus reuteri, Ruminococcus, Lactococcus lactis, Streptococcus thermophilus, Streptococcus salivarius* and *Christensenellaceae* family.

For example, the at least one probiotic strain can be chosen from *Akkermansia muciniphila, Bifidobacterium animalis, Lactobaccilus acidophilus, Lactococcus lactis, Ruminococcus* and *Christensenellaceae* family.

Example 1

Preparation of a Composition (Composition 1) Comprising Compound IV.

Composition 1 comprising compound IV, was prepared by reacting 1 kg of EPA concentrated fish oil (ethyl ester form) with 0.27 kg of glycerol with 0.05 kg of Novozym 435 (lipase) in 2 kg of acetone at 50° C. for 4 h. The lipase was filtered, the acetone was removed in vacuo and the mixture was allowed to stand for phase separation. The lower unreacted glycerol phase was removed to give 1 kg of the final composition 1 comprising compound IV, unreacted ethyl ester and small amount of diglycerides and triglyceride.

Example 2

Composition 1 Increase the Amount of *Akkermansia muciniphila* in Gut Microbita

Data from a prostate cancer mouse model showed increased of *Akkermansia muciniphila* in fecal samples of a lipid formulation containing composition 1-fed animals (FIG. 1B). The presence of *Akkermansia* is believed to stimulate immunotherapy response in cancer patients. In addition, mouse prostate tumor-derived as well as gut-derived microbiota from lipid formulation containing composition 1-treated animals showed reduced *Bacteroides fragilis* (FIG. 1C, 1D). *B. fragilis* can produce a toxin that damages host epithelial cells.

Example 2

Composition 1 Modulate the Gut Microbita in a Phase II Human Clinical Trial.

Figure 2:
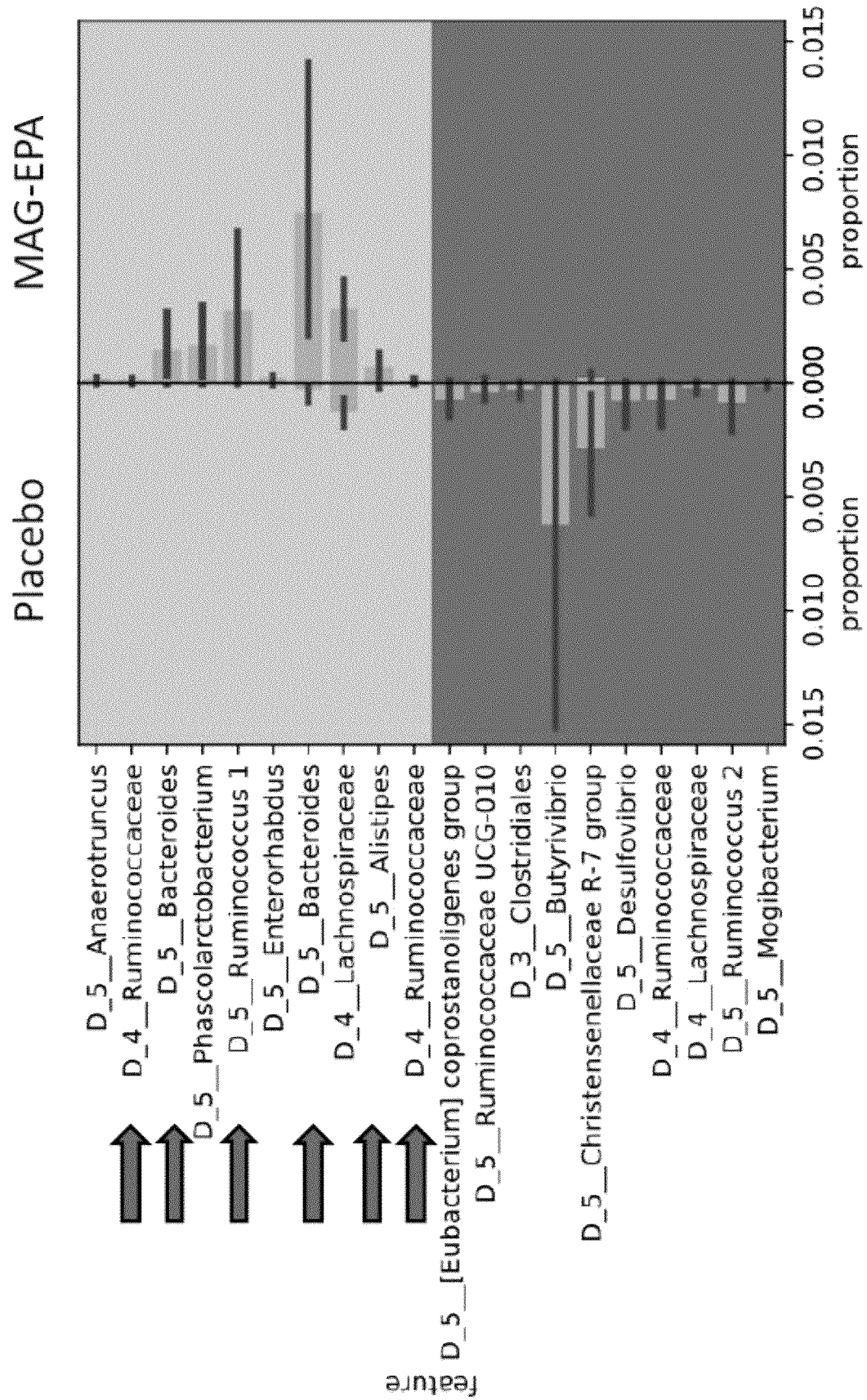
FIG. 2 represents the 16S rDNA sequencing of gut-derived microbiota. N=45 participating to a clinical trial comparing daily composition 1 supplementation (MAG-EPA) versus placebo for 6-8 weeks. Relative abundance of bacteria enriched in both groups+/−SEM are represented. Most bacteria overrepresented in gut-derived microbiota of composition 1 group compared to placebo (arrows) have already been associated with favorable clinical response.

45 patients were randomized to either composition 1 or a placebo for 6-8 weeks before prostatectomy for prostate cancer. 16srRNA analyses showed striking changes in the composition of the gut microbiota of the lipid formulation containing composition 1-treated patients (FIG. 2), in particular an increased abundance of *Ruminococcus* and *Alistipes*, associated in other studies with favourable response to immunotherapy While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present document and including such departures from the present disclosure as come within known or customary practice within the art to which the present document pertains and as may be applied to the features hereinbefore set forth, and as follows in the scope of the appended claims.

What is claimed is:

1. A method of using a composition comprising at least one compound chosen from compound of formula (I), compound of formula (II), compound of formula (III) and compound of formula (IV):

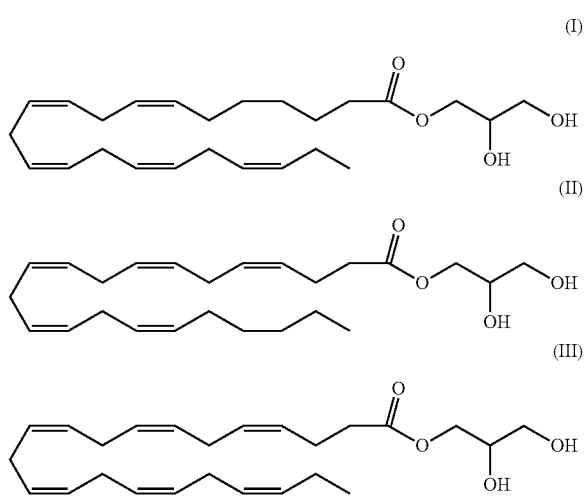

(IV)

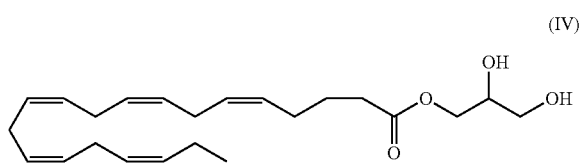

said method comprising administering an effective amount of the composition comprising said at least one compound as a prebiotic, wherein said administration increases at least one probiotic strain selected from *Akkermansia muciniphila, Bifidobacterium animalis, Lactobaccilus acidophilus, Lactococcus lactis*, and *Ruminococcus*.

2. A method for modulating gut microbiota of a subject in need thereof comprising administering to the subject an effective amount of a composition comprising at least one compound chosen from compound of formula (I), compound of formula (II), compound of formula (III) and compound of formula (IV):

(I)

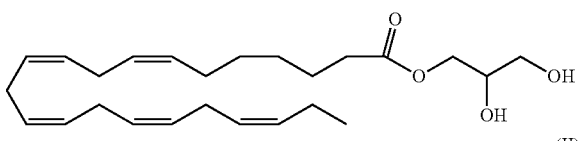

(II)

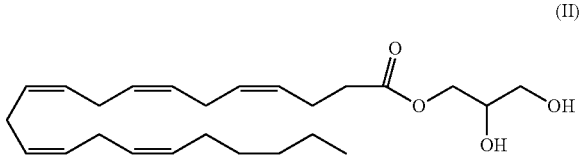

(III)

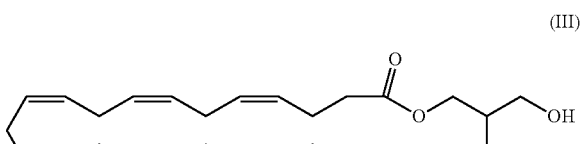

(IV)

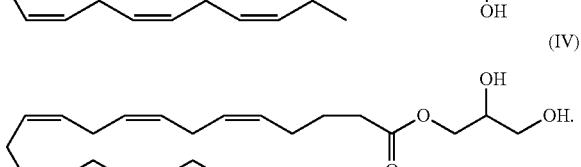

wherein said administration increases at least one probiotic strain selected from *Akkermansia muciniphila, Bifidobacterium animalis, Lactobaccilus acidophilus, Lactococcus lactis*, and *Ruminococcus*.

3. A method for enhancing population of at least one probiotic strain of a subject in need thereof comprising administering to the subject an effective amount of a composition comprising at least one compound chosen from compound of formula (I), compound of formula (II), compound of formula (III) and compound of formula (IV):

(I)

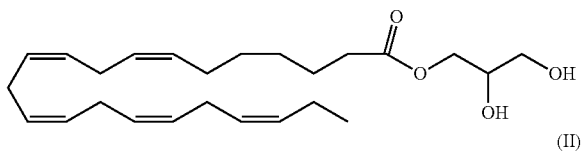

(II)

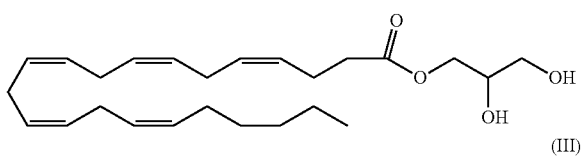

(III)

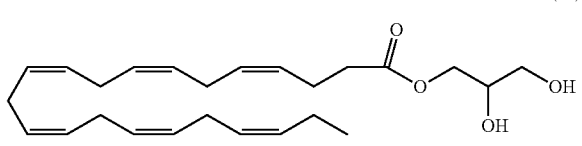

(IV)

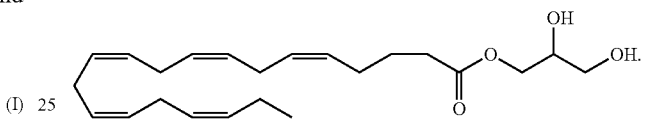

wherein said probiotic strain is selected from *Akkermansia muciniphila, Bifidobacterium animalis, Lactobaccilus acidophilus, Lactococcus lactis*, and *Ruminococcus*.

4. The method of claim 2, wherein said at least one compound is said compound of formula (I).

5. The method of claim 2, wherein said at least one compound is said compound of formula (II).

6. The method of claim 2, wherein said at least one compound is said compound of formula (III).

7. The method of claim 2, wherein said at least one compound is said compound of formula (IV).

8. The method of claim 2, wherein said at least one compound is said compound of formula (I), said compound of formula (III) and said compound of formula (IV).

9. The method of claim 2, wherein said at least one compound is said compound of formula (I) and said compound of formula (IV).

10. The method of claim 2, wherein said at least one compound is said compound of formula (I) and said compound of formula (III).

11. The method of claim 2, wherein said at least one compound is said compound of formula (III) and said compound of formula (IV).

12. The method of claim 2, wherein said at least one compound chosen from compound of formula (I), compound of formula (II), compound of formula (III) and compound of formula (IV) is administered in combination with at least one lipid.

13. The method of claim 2, wherein said at least one lipid and said at least one compound are administered simultaneously.

14. The method of claim 2, wherein said at least one lipid and said at least one compound are administered separately.

* * * * *